United States Patent [19]

Edwards et al.

[11] Patent Number: 5,173,430
[45] Date of Patent: Dec. 22, 1992

[54] METHOD FOR DETERMINING THE NUTRITIONAL VALUE OF VEGETABLE MATERIALS

[76] Inventors: David J. Edwards, Ridge Cottage, Pertenhall, Bedfordshire MK44 AAX; Philip J. Evans, 5 Dove Road, Bedford; Christopher P. Freeman, Meadowbank, Pavenham Road, Felmersham, Bedford MK43 7EX; Geoffrey P. Gray, 54 Oxhey Road, Oxhey, Watford, Herts WD1 4QQ; Robert E. Matthews, 7D Tavistock Road, Westbourne Park, London W11 1AT; Clifford A. Smith, 19 Harvey Road, Rushden, Northamptonshire NN10 9JY; Richard S. Thom, 47 Princess Road, London SW19 8RA, all of England

[21] Appl. No.: 643,106

[22] Filed: Jan. 22, 1991

Related U.S. Application Data

[63] Continuation of Ser. No. 259,514, Oct. 18, 1988, abandoned.

[51] Int. Cl.$^5$ .............................................. C01N 33/02
[52] U.S. Cl. ........................................ 436/20; 436/129; 436/165; 436/177; 426/231; 426/636
[58] Field of Search ................. 436/20, 129, 164, 165, 436/175, 177; 426/231, 135, 636

[56] References Cited

U.S. PATENT DOCUMENTS 4,615,891 10/1986 Nocek .................................. 426/231
4,617,276 10/1986 Nocek ................................... 436/20

OTHER PUBLICATIONS

Perkins, A. E., "Some Chemical Determinations Useful in Silage Studies." J. Dairy Science vol. 24 1944 pp. 512–513.

Baertsche, S. R., "Short Rotation, Hardwood Tree Biomass as Potential Ruminant Feed." J. Animal Science 1986, 63(6) p. 2028.

Primary Examiner—James C. Housel
Assistant Examiner—David Redding
Attorney, Agent, or Firm—Cushman, Darby & Cushman

[57] ABSTRACT

In a method for determining the dry matter content and nutritional value of moist vegetable material, such as silage, liquor is expressed from a sample of known quantity by applying thereto a reproducible pressure regime, the quantity of expressed liquor is measured, and the expressed liquor is analyzed for parameters, such as pH, ammonia, lactic acid, free sugar and alpha-amino nitrogen, from which the nutritional value can be estimated by regression. The nutritional value of silage can be expressed in terms of its fermentability in the rumen. The invention includes a portable facility for use in 'on farm' analysis of silage to determine its nutritional value.

4 Claims, 4 Drawing Sheets

METHOD FOR DETERMINING THE NUTRITIONAL VALUE OF VEGETABLE MATERIALS

This is a continuation of application Ser. No. 07/259,514, filed on Oct. 18, 1988, which was abandoned upon the filing thereof.

The present invention relates to analytical procedures applicable to solid materials having high moisture contents, to equipment for use in such procedures, and to the application of the results of such procedures.

The present invention is particularly applicable to the analysis of moist vegetable material such as silage, grass, fruit and vegetable crops. The invention will be particularly described in relation to the analysis of silage but the skilled reader will appreciate its wider implications.

BACKGROUND OF THE INVENTION

Silage is traditionally produced on individual farms from plant material that the farmer has available. The starting material can include any one or more of the conventional forage plants, such as grass, maize and legumes. Not only is the quality of such starting material variable and unpredictable, but also the conditions under which the farmer produces the silage can differ from one farm to another. The nutritional properties of the resulting silage are therefore very variable.

Silage is used principally as winter forage for animals, such as cattle, and usually needs to be supplemented by commercially available compound feedstuffs. To provide the animals with a balanced diet, the quantity and composition of the compound feedstuff needs to be chosen carefully. Before this choice can be made, the nutritional value of the silage must be known.

Techniques are already available for performing quite detailed analyses of silage, but these techniques are cumbersome and can only be performed satisfactorily in properly equipped laboratories. It is therefore standard practice for silage samples to be sent to appropriate central laboratories from which the required analytical data becomes available only after several days or perhaps weeks.

SUMMARY OF THE INVENTION

One object of the present invention is to provide an analytical procedure that can be performed directly on a farm, for example by a visiting agricultural advisor, and which can provide immediate data on the nutritional value of moist material such as silage. However, although special emphasis will be placed on this objective, it will be appreciated that the invention can be applied in other situations, and indeed can be useful in a laboratory.

The invention provides a method for determining the dry matter content of moist vegetable material such as silage, grass, fruit and vegetable crops, wherein a sample of the moist vegetable material of known quantity is subjected to a reproducible pressure regime to express liquor therefrom, and the dry matter content of the original sample is estimated by regression from the quantity of expressed liquor.

The invention also provides method for determining the nutritional value of moist vegetable material, such as silage, grass, fruit, vegetable crops and the like, wherein liquor is expressed from a sample thereof of known quantity by applying thereto a reproducible pressure regime, and the expressed liquor is analysed for parameters from which the nutritional value can be estimated by regression.

The invention therefore provides a method for preparing silage liquor for analysis. A silage sample of known (preferably predetermined) quantity (e.g. mass, or less preferably volume) is subjected to a reproducible pressure regime to express liquor from the silage. Preferably the applied pressure is raised to, but is not permitted to exceed, a predetermined maximum. Preferably the expressed liquor is collected in a manner such that its quantity, preferably its volume, can be measured.

As a practical matter, in the interest of greater accuracy, the silage sample should not be compressed too rapidly. A more thorough expression of liquor is achieved by a relatively slow, progressive increase in pressure. In the typical practical situation, using for example a silage sample of 20–50 ml or 20–50 gm, the increase of pressure should preferably be applied progressively over a period of at least half a minute, and preferably over a period of about one minute. In general, the maximum applied pressure necessary to express the liquor from a silage sample of this quantity is not likely to exceed about 10 Kilo-Newtons (KN), and more usually will lie in the range of about 1 to about 5 KN.

The invention further provides a method for estimating the nutritional value of silage, in which method liquor is expressed from a silage sample of known quantity using a method as set forth above and the dry matter content of the silage is determined, and the expressed liquor is analysed to determine one or more of the following parameters:

a) the lactic acid concentration of the expressed liquor;
b) the ammonia concentration of the expressed liquor;
c) the pH of the expressed liquor;
d) the concentration of free sugars in the expressed liquor; and
e) the alpha-amino nitrogen concentration in the expressed liquor;

the nutritional value of the silage being estimated from a combination of the estimated dry matter content of the silage and the measured liquor parameters by regression. Preferably the amount of expressed liquor is used to estimate the dry matter content of the silage by regression, although the dry matter content could alternatively be measured using conventional laboratory techniques, such as desiccation.

Silage undergoes "fermentation" in the rumen, and the extent and rapidity of such fermentation is an important nutritional factor. Various organic acids are produced during the course of normal rumen fermentation, and if the rate of fermentation of the silage is too rapid, the accumulation of acid can cause the rumen pH to fall. In dairy cattle, at low rumen pH the bacterial population in the rumen changes, and this leads to undesirable metabolic changes. It is a further object of the present invention to provide methods for determining the likely rapidity of rumen fermentation of a given silage, so that in combination with appropriate complementary feedstuffs a diet can be formulated in which the risk of excessive acid accumulation in the rumen can be minimised.

There are three major components of silage which exert a significant influence on the accumulation of acid in the rumen. These are: free sugars (i.e. soluble carbohydrates); rumen-degradable polysaccharides (including hemicellulose); and lactic acid.

A reliable guide to the fermentability of silage cannot be derived by measuring just one of these parameters. Due importance has to be attached to all three. The precise manner in which these factors are combined to give a measure of the fermentability of the silage is largely a matter of choice. We have found, however, that in practice the sum of these three components in the silage (expressed as a percentage of the total dry matter in the silage) can be used as an indication of the fermentability of the silage. For the purposes of the present specification, we shall refer to this sum as the "Fermentation Index" (FI). If the FI has a value greater than 20, we regard the silage as being likely to ferment rapidly in the rumen.

The importance of rumen-degradable hemicellulose has not previously been recognised as an indication of grass silage quality. An important aspect of the invention is a method for estimating silage quality including the step of measuring, directly or indirectly, the rumen-degradable hemicellulose content of a silage sample.

The above parameters can be determined absolutely using sophisticated laboratory techniques. Rumen-degradable hemicellulose can be measured by the technique described by Mehrez et al in *J. Agric. Sci. Cambridge*, 1977 Vol. 88 page 645. However, a good approximation for the fermentation index can be inferred from the practical determination of other factors, such as the total dry matter content of the silage, the pH of the silage liquor, and the concentrations of lactic acid, free sugars, ammonia and alpha-amino nitrogen in liquor that has been expressed from a silage sample under controlled conditions.

We have found that if liquor is expressed from a predetermined quantity of silage under reproducible pressure conditions, there is a very good correlation between the quantity of the liquor so expressed and the dry matter content of the original silage sample. The precise relationship between the quantity of expressed liquor and the original dry matter content is a function both of the quantity of the silage sample chosen and also the pressure regime chosen, especially the maximum pressure applied. By chosing constant (i.e. thoroughly reproducible) circumstances, and by performing a large number of control experiments involving subjecting samples of different silages of known dry matter content to the constant circumstances, the appropriate relationship between the quantity of expressed liquor and the dry matter content can be determined. Purely by way of example only, we can say that if a loosely packed volume of silage occupying 40 ml is subjected to pressure which is increased from zero applied pressure up to, but not exceeding, about 4 Kilo-Newtons, achieved by the use of a device as described below in Example 1 embodying a torque wrench set at 5.4 Newton-meters (Nm), a good approximation of the dry matter content of the loosely packed silage sample prior to the application of any pressure can be derived from the relationship $$Dry\ matter\ (DM) = 35.4 - (1.3 \times Vol)$$

where Vol is the volume of the expressed liquor.

A relationship of similar form, but with different numerical constants, will be found empirically if a predetermined mass of silage, rather than a predetermined volume of silage, is subjected to a similar controlled compression and the volume of expressed liquor measured. It is also possible to measure the quantity of expressed liquor in terms of its mass, but this is less convenient and is not preferred.

If desired, as a further refinement, the quantity, preferably the volume, of the residual compressed silage sample is measured and used in the regression analysis as an additional term.

The dry matter content of silage is widely recognised as being a very important parameter in determining the silage quality. The dry matter content alone, however, is not generally regarded as a sufficient indication. Importance is also attached to the parameters of crude protein (CP) expressed as a percentage of the total dry matter, and also the parameter of metabolisable energy (ME) which is normally expressed as MJ/KgDM. By subjecting silage samples to the analytical method of the invention as hereinbefore set forth, good approximations of CP and ME can be determined. As with the approximation of the dry matter content, suitable correlations can be derived from repeated experiments with a range of silage samples under controlled conditions. In each instance the CP and ME of the original sample are determined also by routine conventional laboratory methods, as reference points from which to derive appropriate regression equations.

Taking again, for the purposes of example only, a 40 ml volume of loosely packed silage and subjecting this to a pressure increasing up to but not exceeding about 4 KN and thereafter determining the lactic acid and ammonia concentrations (gm per 100 gm of liquor) in the expressed liquor together with the pH of the expressed liquor, the CP can be estimated from the following relationship:

$$CP\ (\% DM) = 13.73 + (0.92 \times LACL) - (0.47 \times DM) + (2.13 \times pH) - (53.36 \times NH3L) + (3.30 \times [NH3L \times DM])$$

where LACL = lactic acid percentage in the expressed liquor, and NH3L = ammonia percentage in expressed liquor.

For the same experimental conditions, the ME value of the original silage sample can be estimated from the relationship:

$$ME = 10.0 + (0.1 \times LACL) + (0.02 \times DM) - (0.24 \times pH) + (0.05 \times [NH3L \times DM])$$

It must be emphasised again that the relationships set forth above have been determined empirically from repeated experiments using a 40 ml volume of silage and the experimental conditions of Example 2 below. These experimental conditions are entirely a matter of choice. If different conditions are chosen, for example a greater or smaller volume of silage or a greater or lesser maximum pressure, similar relationships will prevail for DM, CP and ME but the numerical values of the constants in the above relationships may be very different. These must be determined by repeated control experiments using the precise conditions chosen. Although somewhat laborious, such experiments are entirely a routine matter. The relationships themselves can be determined from the experimental results using well-established mathematical procedures. If desired, additional terms can be included in the regression analysis, such as free sugar content and alpha-amino nitrogen.

The same proviso concerning the experimental conditions is true for equations from which the fermentation index can be derived. Here it is preferable to include all 5 parameters in the analysis. Purely by way of example only, if 32 gm of loosely-packed silage is subjected to pressure which is increased from zero applied pressure up to, but not exceeding, about 4 KN a regression equation from which a good approximation of the fermentation index can be derived is as follows:

$$FI\ (\%\ DM) = 95.96 - (19.01 \times pH) - (17.99 \times LACL) + (14.77 \times FSL) - (222.69 \times NH3L) + (327.18 \times TL) - (3.86 \times DM) - (248.52 \times TL \times TL) + (4.85 \times pH \times LACL) + (50.49 \times pH \times NH3L) + (0.43 \times FSL \times DM) - (49.63 \times pH \times TL) - (5.96 \times pH \times FSL) + (0.78 \times pH \times DM)$$

where
- DM = dry matter content of silage sample
- pH = pH of expressed liquor
- LACL = lactic acid content of expressed liquor
- NH3L = ammonia content of expressed liquor
- TL = alpha-amino nitrogen content of expressed liquor
- FSL = free sugar content of expressed liquor Again it must be stressed that such a formula is only appropriate for these precise experimental conditions and will be subject to considerable variation if these conditions are changed. Standard repeatable conditions have to be selected, and an appropriate regression equation then determined from repeated experiments.

An alternative regression equation, appropriate for the same experimental conditions, from which a good approximation of the fermentation index can be derived is:

$$FI\ (\%\ DM) = 27.86 - (0.09 \times DM) - (4.93 \times pH) + (124 \times TL) - (15.56 \times FSL) + (6.91 \times LACL) - (162.37 \times NH3L) - (244.07 \times TL \times TL) + (1.12 \times DM \times FSL) - (2.59 \times FSL \times FSL) - (0.35 \times DM \times LACL) - (44.85 \times FSL \times NH3L) + (23.91 \times LACL \times NH3L) + (28.29 \times pH \times NH3L)$$

where the terms have the same significance as in the previous equation.

When all five parameters are measured, we have found that it is possible to devise more complex regression equations from which better approximations of crude protein and metabolisable energy can be derived. Purely by way of example, again taking a 32 gm silage sample and applying a maximum pressure of 4 KN, a regression equation from which an approximation for crude protein can be derived is:

$$CP\ (\%\ DM) = 2.89 + (1.82 \times pH) + (0.003 \times LACL) + (2.55 \times FSL) + (52.47 \times NH3L) + (52.78 \times TL) - (0.26 \times DM) - (251.63 \times NH3L \times TL) + (6.63 \times LACL \times NH3L) - (0.82 \times LACL \times FSL).$$

Similarly, for the same experimental conditions, a regression equation from which an approximation of metabolisable energy can be derived is:

$$ME\ (MJ/Kg) = 11.22 - (0.48 \times pH) + (0.88 \times LACL) + (0.71 \times FSL) - (5.1 \times NH3L) + (5.15 \times TL) - (0.04 \times DM) - (0.13 \times FSL \times LACL) - (15.68 \times NH3L \times NH3L) + (2.02 \times pH \times NH3L).$$

The parameters of the liquor mentioned above (lactic acid, ammonia, etc) can be determined by a wide range of analytical techniques already available. Many of these techniques can be applied in the context of the invention. Bearing in mind that it is an objective of the invention to provide a method of analysis that can be performed outside a laboratory (e.g. on a farm), and which therefore should be readily transportable and usable without complicated procedure, it is preferable that the analytical techniques applied to the expressed liquor should be:

a) simple and straight-forward;
b) involve reagents which are non-toxic, safe and few in number (preferably only one); and
c) sensitive, rapid and effective at ambient temperature.

Typical analytical techniques that can be used to determine the lactic acid concentration in the expressed liquor are colorimetric methods for example, using flow injection analyses based on ferric chloride/hydrochloric acid or p-hydroxydiphenyl/concentrated sulphuric acid). Alternatives are UV-enzymic analysis and volumetric analysis.

Analytical methods that are available for determining ammonia concentration include for example colorimetric methods based on Nessler's reagent ($HgI_2/KI$) or phenol/hypo-chlorite. Alternatives are ion-specific electrodes, micro diffusion techniques, nephelometry (turbidimetry), distillation and titration (volumetric) and UV-enzymic analyses.

Methods for determining pH which can be applied to the expressed liquor include liquid indicators which measure visually or by colorimetry, pH meters, and pH papers/strips.

The concentration of free sugars in the expressed liquor can be determined using the method described by Clegg in *J. Sci. Fd. Agric.*, 1965, Vol 7, page 40. Reducing sugars in alkaline solution reduce the yellow coloured ferricyanide ion to the colourless ferrocyanide ion. This reaction is normally carried out with heat, but we have found that it is possible to catalyse the reaction with nickel so that it proceeds rapidly at ambient temperature. This enables the sugar determination to be conducted in an "on farm" apparatus. For example, 200 $\mu$l of diluted ($\times 500$) expressed silage liquor can be added to 50 $\mu$l 0.4% potassium ferricyanide in 10% sodium hydroxide solution plus 6 $\mu$g nickel chloride.

Alpha-amino nitrogen can be estimated by reaction with 2,4,6-trinitrobenzene sulphonic acid (TNBS) which reacts with the primary amine groups to give a yellow coloured complex. The reaction is pH dependent and is adjusted to pH 9–10 by the addition of borate buffer according to the procedure of Okuyama et al in *J. Biochem (Tokyo)*, 1960, Vol 47, pages 454 and 654. In a typical practical situation, 200 $\mu$l of diluted expressed silage liquor is added to 50 $\mu$l 0.06% TNBS solution plus 1% sodium tetraborate in 5% methyl alcohol/water.

In a particular preferred embodiment of the invention in which one or more of the above parameters are measured, all of the reactions employed give products which absorb at approximately the same light wavelength so enabling the required analytical data to be obtained using a very simple common optical measurement system. For example, lactic acid can be determined by reaction with ferric chloride/ hydrochloric acid to produce a colour which typically has an absorption of approximately 415 $\mu$. The ammonia concentration can be determined using Nessler's reagent and the pH can be determined by reaction with methyl red. The other preferred analytical reactions, for free sugars and alpha-amino nitrogen, described above also give products that can be estimated readily at about this same wavelength.

To facilitate the chemical analysis, it may be advantageous to dilute the expressed liquor. Small scale dilution equipment is readily available and can be adapted easily to form part of a transportable analytical facility. Dilution pumps are particularly suitable.

Conveniently, small predetermined metered volumes of the expressed liquor (diluted as necessary) can be added to an array of micro-titre wells which already contain appropriate quantities of the chemical reagents necessary for the performance of the wet chemical analysis. Such reagents can be pre-dosed into the individual wells in liquid form, e.g. in aqueous solution. Alternatively, the reagents can be added in dry soluble form, or dried in situ for example by freeze-drying. In any embodiment, it is preferable to seal the pre-dosed wells with a readily-removable or readily-breakable cover, such as a tear-off strip, to prevent loss or contamination of the reagents prior to use.

The analytical results can be determined by comparison with standard data, e.g. by eye using colour charts or preferably by a photometric technique.

The silage quality can be determined manually, e.g. by calculation or by reference to tabulated correlations, using the derived relationships, or if desired the value can be derived using a micro-processor programmed with regression equations.

DESCRIPTION OF THE PREFERRED EMBODIMENTS

A preferred embodiment of the invention is an apparatus comprising:

(a) means for applying to a silage sample of known quantity, pressure up to but not exceeding a predetermined maximum to express liquor therefrom;

(b) means for determining the quantity of the liquor so expressed;

(c) optionally, means for determining the quantity of the residual compressed silage sample;

(d) optionally, means for diluting the expressed liquor; and (e) means for metering predetermined small volumes of the expressed liquor (diluted if required) into one or more receptacles in which wet chemical analysis can be performed.

The invention also provides a portable facility for use in 'on farm' analysis of silage to determine its nutritional value, comprising apparatus as defined above, together with one or more receptacles in which the chemical analyses can be conducted, reagents appropriate for the chemical analyses, means for determining the results of the chemical analyses and means for deriving therefrom an indication of the nutritional value. Preferably the receptacles comprise a linked array of wells, and preferably the wells are predosed with appropriate reagents.

The invention also provides a method of formulating for ruminant animals a complete diet involving silage, in which method the rumen fermentability of the silage is determined and complementary feedstuffs are administered to the animals depending upon whether the silage fermentability is regarded as being high or low. Using the "Fermentation Index" relationship hereinbefore described, a highly fermentable silage would be one having an FI value greater than 20. When the silage is regarded as being highly fermentable, the complementary feedstuff should be characterised by comparatively reduced levels of rapidly fermentable starch and sugars; increased levels of digestible fibre (slowly digestible cellulose); enhanced buffering capacity e.g. through the inclusion of materials having high levels of cation exchange capacity; and reduced levels of rumen degradable protein (RDP) and elevated levels of comparatively undegradable protein (UDP).

Thus, for example, it is possible to devise a complementary feeding matrix as shown below.

| Conventional Silage Quality | Fermentation Index | |
|---|---|---|
| | Low (<20) | High (>20) |
| | Complementary Feed Formulation | |
| GOOD | *High fermentation characteristics | *Low fermentation characteristics |
| (High ME/CP and low NH3-N) | *Average UDP | *High digestible fibre |
| D value greater than 60 | *Average buffering | *High UDP/Low RDP |
| | | *High buffering |
| | (ME 13.5 MJ/Kg DM) | |
| MEDIUM | *High fermentation characteristics | *Low fermentation characteristics |
| (Low ME/CP/DM and low NH3-N) | *Average UDP | *High digesible fibre |
| D value lower than 60 | *Average buffering | *High UDP/Low RDP |
| | | *High buffering |
| | (ME 14.5-15 MJ/kg DM) | |

D value = digestibility (%) of silage organic matter

The D value can be determined using the recognised relationship between it and ME, namely:

$$D=(ME-3.2)/0.11$$

This is based on the relationship recommended by the UK Ministry of Agriculture, Fisheries and Food, *ADAS Reference Book No.* 433 "Energy Allowances and Feeding Systems for Ruminants", 2nd Edn. 1984 (HMSO, London) pg. 73.

By way of example only, an aspects of the invention will now be described with reference to the accompanying drawings.

EXAMPLE 1

Figure 1:
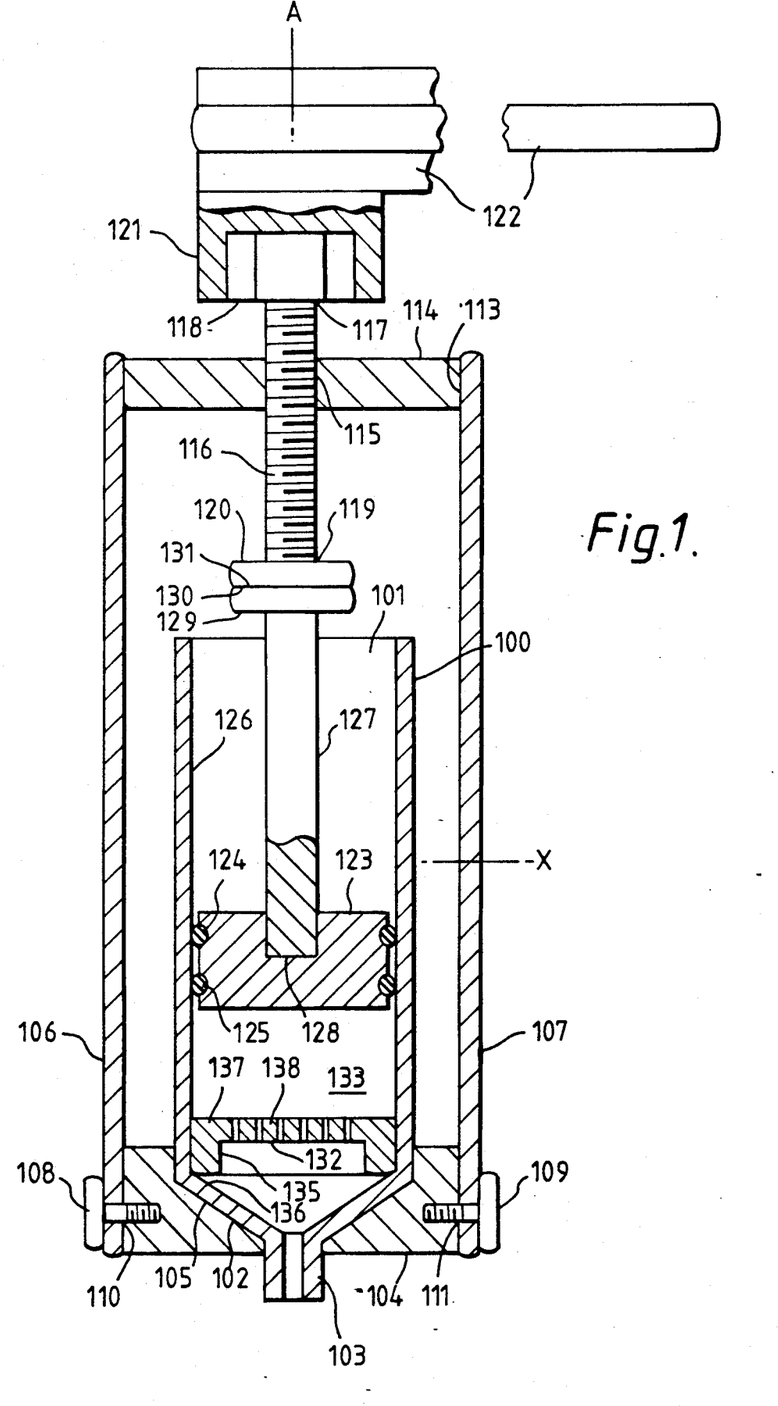
FIG. 1 of the accompanying drawings is a diagrammatic partial cross-sectional elevation of an apparatus that can be used to express liquor from silage during an analytical procedure in accordance with the invention.

FIG. 1 of the accompanying drawings is a diagrammatic partial cross-sectional elevation of an apparatus that can be used to express liquor from silage during an analytical procedure in accordance with the invention.

The apparatus comprises an upright cylindrical vessel 100 open at its top end and 101 having at its bottom end a frustro-conical portion 102 terminating in a short open-ended nozzle 103. Vessel 100 is loosely seated in the centre of a ring-shaped base member 104, the inner face 105 of which is profiled to match the frustro-conical portion 102 of vessel 100. Two side members 106 and 107 are pivotally attached by means of threaded pins 108 and 109 at diametrically opposite sites 110 and 111 on the outside of base member 104. The two side members 106 and 107 extend upwardly from base member 104, parallel to the vessel 100, and are attached to diametrically opposing sites 112 and 113 on the circumference of an upper ring 114 having the same external diameter as base member 104. Base member 104, upper ring 114 and side members 106 and 107 together form a rigid frame-work capable of withstanding considerable vertical pressure, within which frame-work the vessel 100 is seated.

Extending through a threaded central hole 115 in the upper ring 114 is a co-operatively threaded rod 116 terminating at its upper end 117 in a hexagonal bolt head 118. The lower end 119 of threaded rod 116 carries a horizontally mounted disc 120 which is freely rotatable about the longitudinal axis of rod 116. The hexagonal bolt head 118 is engageable with the head 121 of a torque wrench 122.

The cylindrical vessel 100 is fitted with a removable piston 123 which is a tight sliding fit within the vessel and which is fitted with two O-rings 124 and 125 which form a reasonably water-tight seal against the inner surface 126 of the cylindrical vessel 100. As shown in the drawing, a rod 127 extends from the centre 128 of piston 123, upwardly and through the open top 101 of the cylindrical vessel 100 and terminates in a freely rotatable disc 129, the upper surface 130 of which can butt against the lower surface 131 of the disc 120 attached to the threaded rod 116. The cylindrical vessel 100, the piston 127, discs 120 and 129, and threaded rod 116 lie on a common axis A. When the threaded rod 116 is rotated so that it descends through the upper ring 114, a downward force can be applied to the piston 123 via the two discs 120 and 129 and rod 127. If contact between the two 120 and 129 discs is maintained, rotation of the bolt head 118, e.g. by means of the torque wrench 122, can cause piston to be 123 forced downwards into the cylindrical vessel 100.

A filter means 132 is loosely seated inside the lower region 133 of cylindrical vessel 100. This filter means comprises a sleeve 134 of which the outer diameter is slightly smaller than the maximum internal diameter of the vessel 100. The lower end 135 of the sleeve 134 therefore rests against the shoulder 136 formed by the internal surface of the frustro-conical portion 102 of the vessel 100. The upper end 137 of the sleeve is closed by means of a foraminous disc 138.

In operation, piston 123 is removed from the cylindrical vessel 100 and, with the filter means 132 in place at the bottom of the vessel the vessel is loosely packed with silage 35 to a predetermined level arbitrarily indicated by the mark 'X' in the drawing. The vessel is seated in the base member 104 and the piston 123 inserted into the upper end 101 of the cylindrical vessel. The wrench 122 set to a predetermined torque value is applied to the bolt head 118 and the piston forced downwardly into the cylindrical vessel to compress the silage sample. The silage solids are retained by the filter means 132 and expressed liquor is collected from the nozzle 103 in a suitable receptical (not shown).

Figure 2:
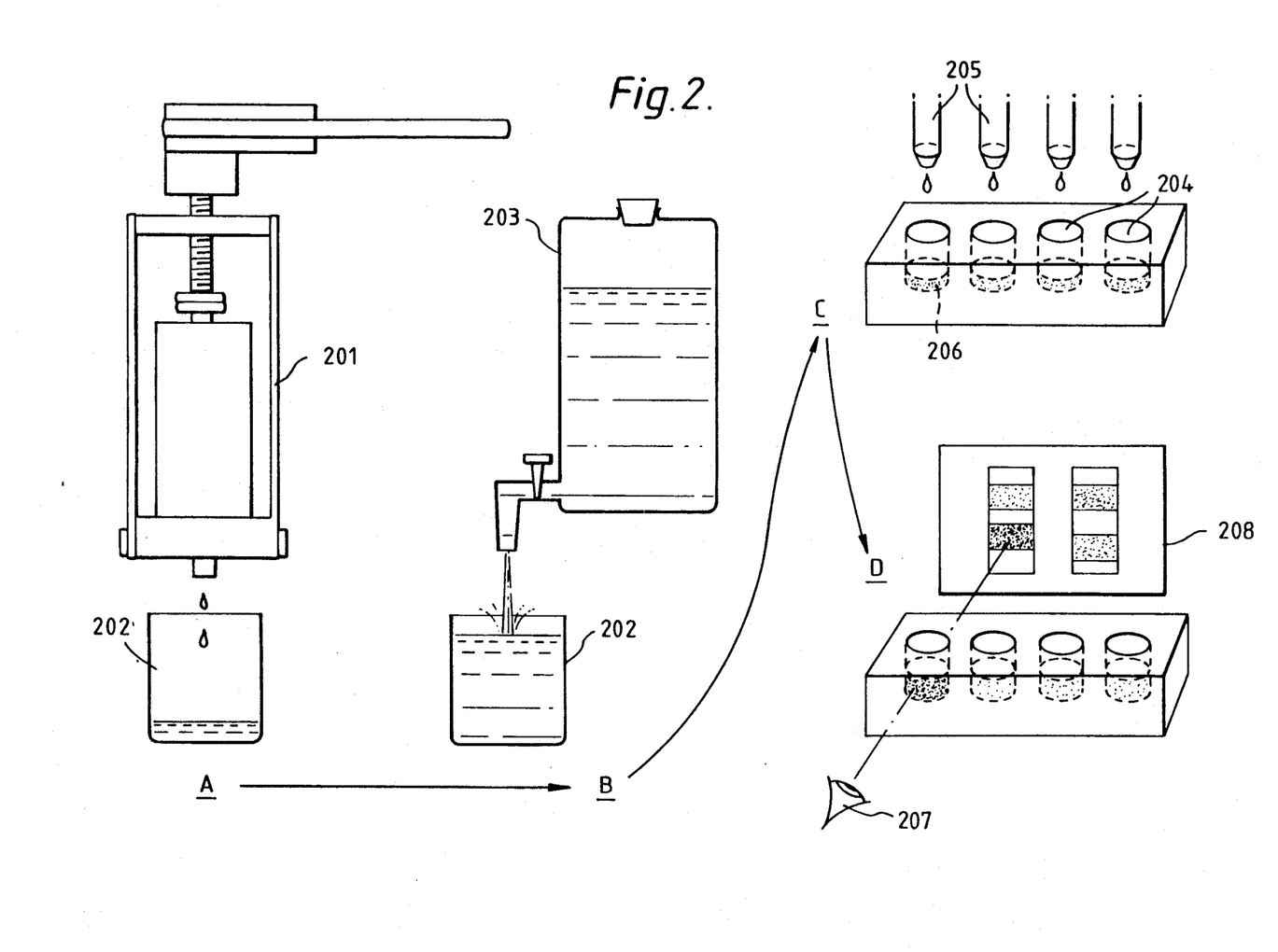
FIG. 2 shows the stages in a typical analytical procedure in accordance with the invention.

FIG. 2 shows the stages in a typical analytical procedure in accordance with the invention.

In Stage A, liquor is expressed from a predetermined volume of silage using an apparatus 201 as just described with reference to FIG. 1. The expressed liquor is collected in a vessel 202 and its volume determined.

In Stage B, the expressed liquor is diluted with, for example, distilled water from a reservoir 203. The expressed liquor may be strongly coloured, or may contain substantial amounts of solid material in the form of finely dispersed particles. These factors could interfere with subsequent chemical analysis, especially if the analytical results are to be assessed optically. Standardised dilution, eg, by a factor of 500, can eliminate these problems.

In Stage C, predetermined volumes of the diluted silage liquor are added to an array of microtiter wells 204 by means of a multiple dosing head 205. Each well already contains appropriate reagents 206 necessary to conduct a specific chemical analysis on the silage liquor.

In Stage D, after the elapse of such time as may be necessary for the analytical reaction to occur, the analytical result is determined. In the instance depicted in the drawing, the analytical reaction produces a colour change or colour formation in the microtiter well and the extent to which the reaction has taken place is judged by eye 207 with reference to a standardised colour chart 208.

EXAMPLE 2

The following typical analytical results demonstrate the effectiveness of the invention.

A silage sample was subjected to the procedure just described, and as a control a sample of the same silage was analysed according to conventional laboratory procedures.

40 ml of silage was compressed to 5.4 Nm torque, and 13 ml of liquor expressed. 20 $\mu$l of expressed liquor was diluted to 10 ml with distilled water. 200 $\mu$l aliquots of the diluted liquor were pipetted into wells each containing 10 $\mu$l of standard reagents, namely:

Ferric chloride/HCL for lactic acid
Nessler's reagent for ammonia
Methyl red for pH
The analytical data found was:
Lactic acid: 3.4 gm/100 ml of undiluted liquor
Ammonia: 0.04 gm/100 ml of undiluted liquor
pH of undiluted liquor: 3.8 units.

Applying the regression equations given earlier, the following properties of the silage were derived. These compare very well with the "actual" values as obtained from the conventional laboratory analysis:

| Parameter | Value estimated using invention | "Actual" (laboratory) value |
|---|---|---|
| Dry Matter (DM) % | 18.9 | 18.6 |
| Crude Protein (CP) % of DM | 16.4 | 16.5 |
| Metabolisable Energy (ME) | 9.9 | 10.0 |

EXAMPLE 3

Figure 3:
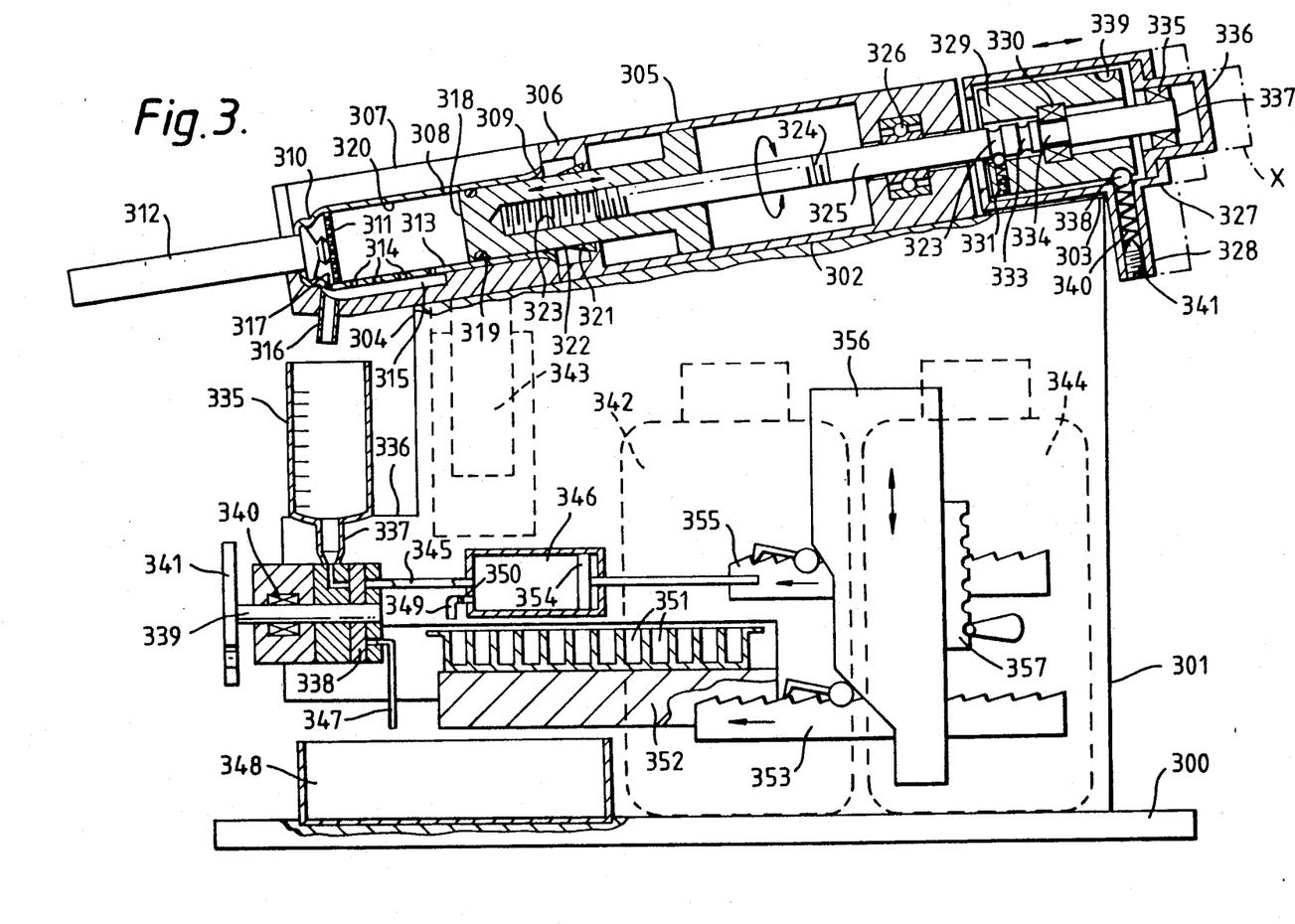
FIG. 3 depicts, in diagrammatic partial cross-sectional side elevation, the general layout of the apparatus.
Figure 4:
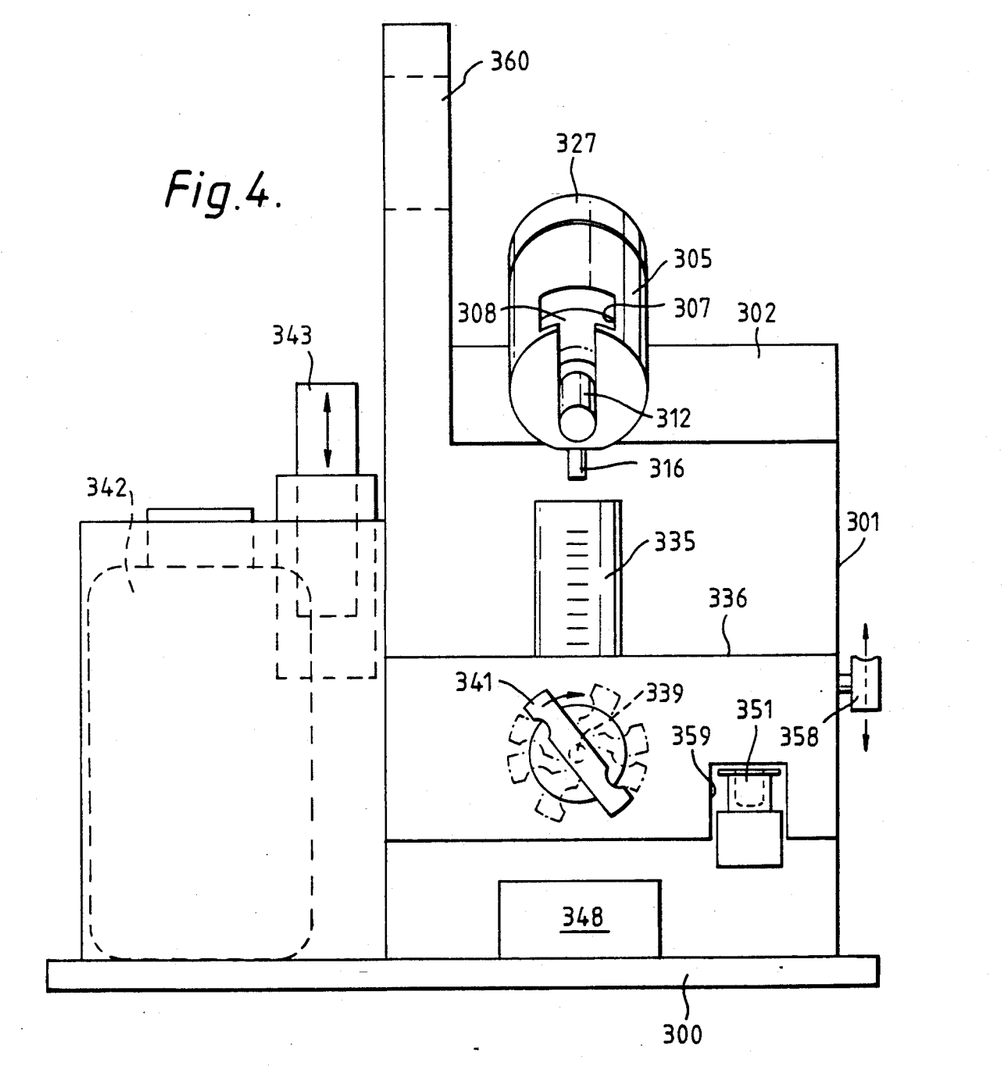
FIG. 4 depicts a front elevation of the apparatus.

This example illustrates, with reference to FIGS. 3 and 4 of the accompanying drawings, a portable apparatus, suitable for use on a farm, in which a sample of silage of known quantity can be compressed to express liquor therefrom, the volume of the liquor can be measured, and a predetermined small quantity of the liquor can be metered into an array of wells for analysis.

FIG. 3 depicts, in diagrammatic partial cross-sectional side elevation, the general layout of the apparatus, and FIG. 4 depicts a front elevation of the apparatus.

Referring to FIG. 3, which shows only the most essential components of the complete apparatus and indicates their inter-relationships in general terms, the apparatus comprises a base 300 capable of supporting the apparatus on a horizontal surface, an outer casing 301 of which the flat upper surface 302 slopes downwardly from the rear 303 towards the front 304 (from right to left as seen in this drawing) and is surmounted by a silage compressing unit 305 which slopes similarly downwards. Silage compressing unit 305 comprises a hollow barrel 306 the forward portion 307 of which is open at the top to permit a silage compression cylinder 308 to be co-axially placed within barrel 306. Silage compression cylinder 308 is open at its rear end 309, and the other closed end 310 accommodates a flat circular filter plate 311 attached to one end of a slidable shaft 312 which projects outwardly from the closed end of cylinder 308 along the axis of the cylinder. Shaft 312 and filter plate 311 together can function as a ram by means of which a compressed silage sample within cylinder 308 can be ejected therefrom if the cylinder has been removed from barrel 306. The lower wall 313 of cylinder 308 is pierced with a plurality of fine orifices 314 through which liquor in a silage sample being compressed within cylinder 308 can escape into a duct 315 in barrel 306 directly beneath cylinder 308, and can flow out of barrel 306 through outlet 316. Similarly, liquor escaping through filter plate 311 can enter duct 315 through orifice 317.

A hollow piston 318 retained within barrel 306 can be slidably inserted into open end 309 of silage compression cylinder 308, and is fitted with an O-ring 319 to provide a liquor-tight seal against the inner surface 320 of cylinder 308. Close to the open end 309 of cylinder 308, a scraper ring 321 is fitted within barrel 306 and contacts the outer surface 322 of piston 318, to clean off any silage particles that may be adhering to the piston. The hollow inside 323 of piston 318 is threaded, and cooperatively engages a forward threaded portion 324 of a long axial shaft 325 which extends backwards from piston 318 to the rear of barrel 306. The location of shaft 325 within barrel 306 is constant, but axial rotation of shaft 325, either clockwise or anti-clockwise, causes piston 318 to slide in or out of cylinder 308. Shaft 325 passes through a thrust bearing 326 and out of the rear end of barrel 306, and into a separate hand-operable winding/torque release mechanism by means of which shaft 325 can be rotated in either direction.

The shaft winding/torque release mechanism comprises a hollow cylindrical body 327 co-axial with shaft 325 and from which a hollow winding handle 328 projects radially. Within body 327 is a co-axially mounted sleeve 329 incorporating a roller clutch 330 which can engage shaft 325. Sleeve 329 also incorporates a position detent mechanism 331 which can engage one of two grooves 332 and 333 in shaft 325 to define two possible positions (forward and rear) of the winding mechanism. A portion 334 of shaft 325 has a reduced diameter, and portion 334 in the forward position of the winding mechanism (as seen in FIG. 3) lies inside roller clutch 330 and prevents roller clutch 330 from engaging shaft 325. When the winding mechanism is in the rear position (indicated by broken line X), roller clutch 330 can engage shaft 325. A second roller clutch 335 is contained in a housing 336 which encases the rear end 337 of shaft 325 and which provides means to rewind shaft 325. Handle 328 incorporates an adjustable ratchet mechanism which engages sleeve 329, essentially comprising a ball detent 338 acting on hemispherical indentations 339 in sleeve 329, the necessary release pressure for the ratchet mechanism being adjustable by means of screw 340 and spring 341 within handle 328. The winding mechanism is depicted in the rewind (forward) position. When the winding mechanism is moved to position X, roller clutch 330 can engage shaft 325; by this means it is possible for the winding mechanism to be used to rotate shaft 325 in either direction at will.

Beneath outlet 316 an open-topped graduated cylinder 335 stands on a ledge 336 projecting forward from casing 301. Expressed liquor can be collected in graduated cylinder 335 and its volume read by eye. From the bottom of graduated cylinder 335 an outlet pipe 337 leads to a four-way valve 338, operated by a shaft 339 passing out of casing 301 via a roller-clutch 340 and terminating in a handle 341. The details of valve 338 are not shown, but its operation enables, when the valve is rotated from a first closed position to first open position, a small predetermined quantity of liquor from graduated cylinder 335 to be run off into the body of the valve. Thereafter, valve 338 can be rotated to a second open position wherein the entrapped liquor can be simultaneously expelled and diluted, using a predetermined quantity of diluent (normally water) from a reservoir container 342 driven by means of dilution pump 343. A spare reservoir container 344 is also provided. The expelled dilute liquor passes through pipe 345 into cylinder 346. Further rotation of valve 338 to another open position enables the valve to be flushed out with further diluent from the same source, the waste liquid passing through pipe 347 into sink 348.

Outlet pipe 349 from cylinder 346, closable by means of ball valve 350, projects over a linked array of wells 351 placed within the apparatus on a carrier 352 drivable by means of a rack mechanism 353. A piston 354 within cylinder 346 is connected to another rack mechanism 355, and both racks are powered by a hand-operable ramp means 356 which can be flipped up and down. Ramp means 356 is fitted with an interlock mechanism 357, and is arranged such that movement of the ramp causes the array of wells 351 and piston 354 to move forward alternately, so that on each occasion that movement of the piston results in a quantity of diluted liquor to be expelled from outlet pipe 349, the next empty well is beneath the outlet.

If desired, the steps of dilution and dispensing can be combined by the use of a common cylinder and discharge mechanism.

Referring to FIG. 4, in which all common reference numerals have the same significance as in FIG. 3, the open upper region 307 of the forward end of barrel 306 can be seen, with the silage compression cylinder 308 lying within the barrel. The four positions of the valve handle 341 are depicted diagrammatically. An external handle 358 by means of which the ramp means can be operated projects from the side of casing 301. The array of wells 351, one end of which can be seen, is inserted into casing 301 via a square aperture 359. Rising from the middle of casing 301 is a carrying handle 360 (not shown in FIG. 3).

In operation, an array of wells (pre-dosed with reagents if desired) is placed within the casing on the rack mechanism. A silage compression cylinder is loaded with a known quantity (mass or volume) of silage, and placed in the barrel. The winding mechanism is operated in position X to cause the piston to enter the cylinder and compress the silage until the applied pressure reaches the pre-determined maximum and the ratchet effect of the ball detent in the winding mechanism handle causes the winding mechanism to free-wheel on the shaft. Thereafter, the mechanism is pushed forward and the shaft rotated in the opposite direction to withdraw the piston, and the cylinder extracted is from the barrel and the silage plug ejected by means of the ram. The volume of expressed liquor is noted, and the four-way valve operated to cause a diluted quantity of the liquor to be charged into the cylinder. The ramp means is then operated to meter aliquots of the diluted liquor into the wells, which can then be removed from the apparatus for further analysis, for example by being placed in an optical reader linked to a micro-processor programmed to display nutritional properties of the silage sample according to regression equations previously determined.

We claim:

1. A method for determining the nutritional value of silage expressed as a function of it's fermentability in the rumen, which comprises subjecting a known quantity of silage to a reproducible pressure regime to express liquor therefrom, determining the dry matter content of the silage, analyzing the expressed liquor for parameters from which the nutritional value can be determined by regression from the quantity of expressed liquor, said parameters including one or more of the following:
   pH
   lactic acid concentration
   ammonia concentration
   free sugars concentration
   alpha-amino nitrogen concentration,
and calculating the nutritional value of the silage on the basis of said parameters.

2. A method for determining the nutritional value of silage expressed as a function of its fermentability in the rumen, which comprises expressing liquor from a sample of the silage, analyzing the so expressed liquor to determine, either directly or indirectly, its content of soluble carbohydrates, rumen-degradable polysaccarides and lactic acid, and calculating the nutritional value of the silage.

3. A method according to claim 2 wherein the fermentability is expressed as the sum of the three contents, each content being expressed as a percentage of the total dry matter of the silage.

4. A method of formulating a complete diet, including silage, for feeding to ruminant animals, which comprises determining the nutritional value of the silage by a method which comprises subjecting a sample of moist silage to a reproducible pressure regime to express liquor therefrom, measuring the quantity of expressed liquor, and determining the dry matter content of the original sample of silage by regression from the quantity of expressed liquor, determining the nutritional value of said silage, and thereafter formulating a complete diet based on the nutritional value of said silage.

* * * * *